(12) United States Patent
Parker

(10) Patent No.: US 6,519,487 B1
(45) Date of Patent: *Feb. 11, 2003

(54) REUSABLE PULSE OXIMETER PROBE AND DISPOSABLE BANDAGE APPARATUS

(75) Inventor: Brent Parker, Murrieta, CA (US)

(73) Assignee: Sensidyne, Inc., Clearwater, FL (US)

( * ) Notice: Subject to any disclaimer, the term of this patent is extended or adjusted under 35 U.S.C. 154(b) by 68 days.

This patent is subject to a terminal disclaimer.

(21) Appl. No.: 09/679,828

(22) Filed: Oct. 5, 2000

Related U.S. Application Data

(63) Continuation-in-part of application No. 09/289,647, filed on Apr. 12, 1999, now Pat. No. 6,144,868, and a continuation-in-part of application No. 09/417,898, filed on Oct. 14, 1999, now Pat. No. 6,343,224.
(60) Provisional application No. 60/104,332, filed on Oct. 15, 1998.

(51) Int. Cl.[7] .................................................. A61B 5/00
(52) U.S. Cl. ........................................ 600/344; 600/310
(58) Field of Search ................................. 600/310, 322, 600/323, 340, 344

(56) References Cited

U.S. PATENT DOCUMENTS

| | | | |
|---|---|---|---|
| 4,621,643 A | 11/1986 | New, Jr. et al. | |
| 4,685,464 A | 8/1987 | Goldberger et al. | |
| 4,700,708 A | 10/1987 | New, Jr. et al. | |
| 4,830,014 A | 5/1989 | Goodman et al. | |
| 5,090,410 A | 2/1992 | Saper et al. | |
| 5,094,240 A | 3/1992 | Muz | |
| 5,170,786 A | 12/1992 | Thomas et al. | |
| 5,507,286 A | 4/1996 | Solenberger | |
| 5,673,693 A | 10/1997 | Solenberger | |
| 5,678,544 A | 10/1997 | DeLonzor et al. | |
| 5,817,010 A | 10/1998 | Hibl | 600/344 |
| RE36,000 E | 12/1998 | Swedlow et al. | |
| 5,879,373 A | 3/1999 | Röper | 606/344 |
| 6,144,868 A * | 11/2000 | Parker | 600/310 |
| 6,343,224 B1 * | 1/2002 | Parker | 600/310 |

* cited by examiner

*Primary Examiner*—Eric F. Winakur
(74) *Attorney, Agent, or Firm*—Jim Zegeer

(57) ABSTRACT

Pulse oximeter apparatus and method comprising a reusable pulse oximeter probe and a disposable bandage. The bandage has receptacles for receiving and aligning the oximeter's light emitting diode and photocell detector.

17 Claims, 12 Drawing Sheets

REUSABLE PULSE OXIMETER PROBE AND DISPOSABLE BANDAGE APPARATUS

REFERENCE TO RELATED APPLICATION

This application is a continuation in part of patent applications Ser. No. 09/289,647 filed Apr. 12, 1999 now U.S. Pat. No. 6,144,868 and Ser. No. 09/417,898 filed Oct. 14, 1999 now U.S. Pat. No. 6,343,224 both applications being entitled: "Reusable Pulse Oximeter Probe and Disposable Bandage Apparatus." This application claims benefit of provisional application 60/104,332 filed Oct. 15, 1998.

BACKGROUND OF THE INVENTION

The present invention relates to a method of making and affixing a reusable probe to a patient by means of disposable bandage apparatus so that there is no contact between the costly, reusable portion of the probe and the patient. The contaminated bandage apparatus, which is relatively inexpensive, can then be discarded after single patient use and the probe can be re-used with a new bandage apparatus.

Heretofore the use of pulse oximeter probes has been limited to the use of a costly reusable probe, which is contaminated by use on a patient, or cheaper, single-use probes, which, in the aggregate, amount to a considerable expenditure for a health care institution.

Other individuals have attempted to convert single use probes into multi-use probes through a lamination process. In that process, the original adhesive material is removed from the original manufacturer's sensor. The sensor is then laminated in a plastic sheath and the entire sheath is then inserted into a transparent, adhesive-backed sleeve, which is then adhered to a patient. After use, the probe can then be extracted from the sleeve and inserted into a new sleeve for use on another patient.

There are certain disadvantages to this method. Firstly, it is difficult to insert the flexible laminated sensor into a long sleeve. Secondly, the thickness of a laminated sensor inside of a sleeve makes it difficult to bend around, and to stick properly to, a human appendage. Thirdly, transmission and reception of infrared light can be affected by extraneous light entering from the sides of the sleeve. And fourthly, there is some dispute as to the affect on infrared light transmission when passing through the sleeve and the adhesive material coupled thereto.

THE PRESENT INVENTION

The present invention not only solves the problems outlined above, but offers an alternative that is cheap to manufacture and easy to use.

The present invention is directed to improving the form and affixation method of a reusable pulse oximeter sensor. It comprises a reusable pulse oximeter probe with at least one light emitting diode and one photocell detector wherein said emitter and detector are enclosed in plastic housings, one housing having an aperture or radiation transparent window aligned with said emitter, and the other housing having an aperture or radiation transparent window aligned with said detector. Also included is a disposable bandage apparatus which is at least one bandage strip having adhesive on at least a portion of at least one face thereof and at least two plastic receptacles mounted thereon, each receptacle having at least one aperture or radiation transparent window located therein. The probe housings can matedly engage said bandage receptacles and transmit and receive light through the apertures or radiation transparent windows of said mated housings and receptacles, and through the appendage of a patient. The housings of the reusable pulse oximeter probe may also be made of a material selected from plastic, rubber, metal, wood, or other composite material. The receptacles of the disposable bandage apparatus may also be made of a material selected from plastic, rubber, metal, wood, or other composite material. Additionally, the apertures of said receptacles are large enough to accept the tubular protrusions of the housings for the purpose of concentric location and alignment of the housings to the receptacles and the proper transmission and reception of light therethrough. Sandwiched between the adhesive strip and the receptacles attached thereto, are translucent silicone windows or windows of another radiation transparent material for isolation of the reusable probe assembly from the patient. The bandage apparatus may be discarded after single patient use and the reusable probe may be used again on another patient in conjunction with another bandage apparatus. Additionally, the receptacles of the bandage apparatus may have a concave surface on one side thereof in order to seat conformably on a human digit, or they may have a flat surface on at least one side thereof in order to attach conformably to a human foot, nose, or ear. The housings and receptacles also contain "mushroom hook" type hook and loop material for the purpose of adhering and detaching said housings to and from said receptacles. Additionally, the housings and receptacles have recessed areas for adhesion of the "mushroom hook" hook and loop material.

In another embodiment of the invention, the receptacle of the disposable bandage apparatus may be the mushroom hook material itself which may be attached directly to the adhesive strip for the selective engagement of the housings of the probe assembly.

In another embodiment of the invention, the housings of the pulse oximeter probe may be affixed to the receptacles of the disposable bandage apparatus by means of a "ring and groove" type snap-on connector.

In yet another embodiment of the invention, the housings of the reusable pulse oximeter probe may be affixed to the receptacles of the disposable bandage apparatus by means of a "twist and lock" type connector.

In a further embodiment of the invention, the housings of the pulse oximeter probe may be affixed to the receptacles of the disposable bandage apparatus by means of a "threaded flange" type of connector.

Finally, and in the first preferred embodiment of the invention. The light emitting diode and photocell detector of the probe assembly may be mounted in modular housings with locking levers which can engage an indentation or slot in the receptacles of the disposable bandage apparatus and securely lock the housings into proper position within the receptacles, thus allowing the transmission and reception of infrared light through the mated housings and receptacles and through the appendage of a patient.

In another variation of this preferred embodiment of the invention, the levers and indentations are reversed, and the light emitting diode and photocell detector of the probe assembly may be mounted in modular housings having indentations therein, and the receptacles of the disposable bandage apparatus may have the locking lever located on them. In such an embodiment, the locking levers of the bandage receptacles lockingly engage the slots or indentations in the probe housings, thus locking them into place within the receptacles and allowing the transmission and reception of infrared light through the mated probe housings and bandage receptacles, and through the appendage of a patient.

In these modular housing and receptacle embodiments the radiation transparent windows, may be of hard plastic and may be mounted against the skin of a patient, thus being used to secure the receptacles on the opposite side of the bandage strip. This is accomplished by the incorporation of locking levers on the radiation transparent windows which are pushed through holes or slots in the bandage and engage holes in the receptacles mounted on the opposite side of the bandage, thus sandwiching the bandage in between. A foam strip with holes in it may also be adhered to said radiation transparent windows in order for them to rest comfortably on a patient's appendage.

In another variation of the above, the bandage receptacles may be secured to the bandage through the use of small plastic protrusions or "heat stakes" mounted on the receptacles themselves. These protrusions can be pushed through slots in the bandage and can be melted on the other side of the bandage strip by means of an ultrasonic welding machine, thus locking the receptacles into position on the bandage strip. In this embodiment a radiation transparent window may then be adhered to the underside of the bandage strip and the heat stakes and radiation transparent windows may then be overlaid with a foam pad with holes in it, the purpose of which is to allow for the transmission and reception of infrared light through the holes while aiding in patient comfort.

DESCRIPTION OF THE DRAWINGS

The above and other objects and features of the invention will become more clear when considered with the following specifications and accompanying drawings wherein.

DESCRIPTION OF THE REUSABLE PULSE OXIMETER SENSOR

Figure 1:
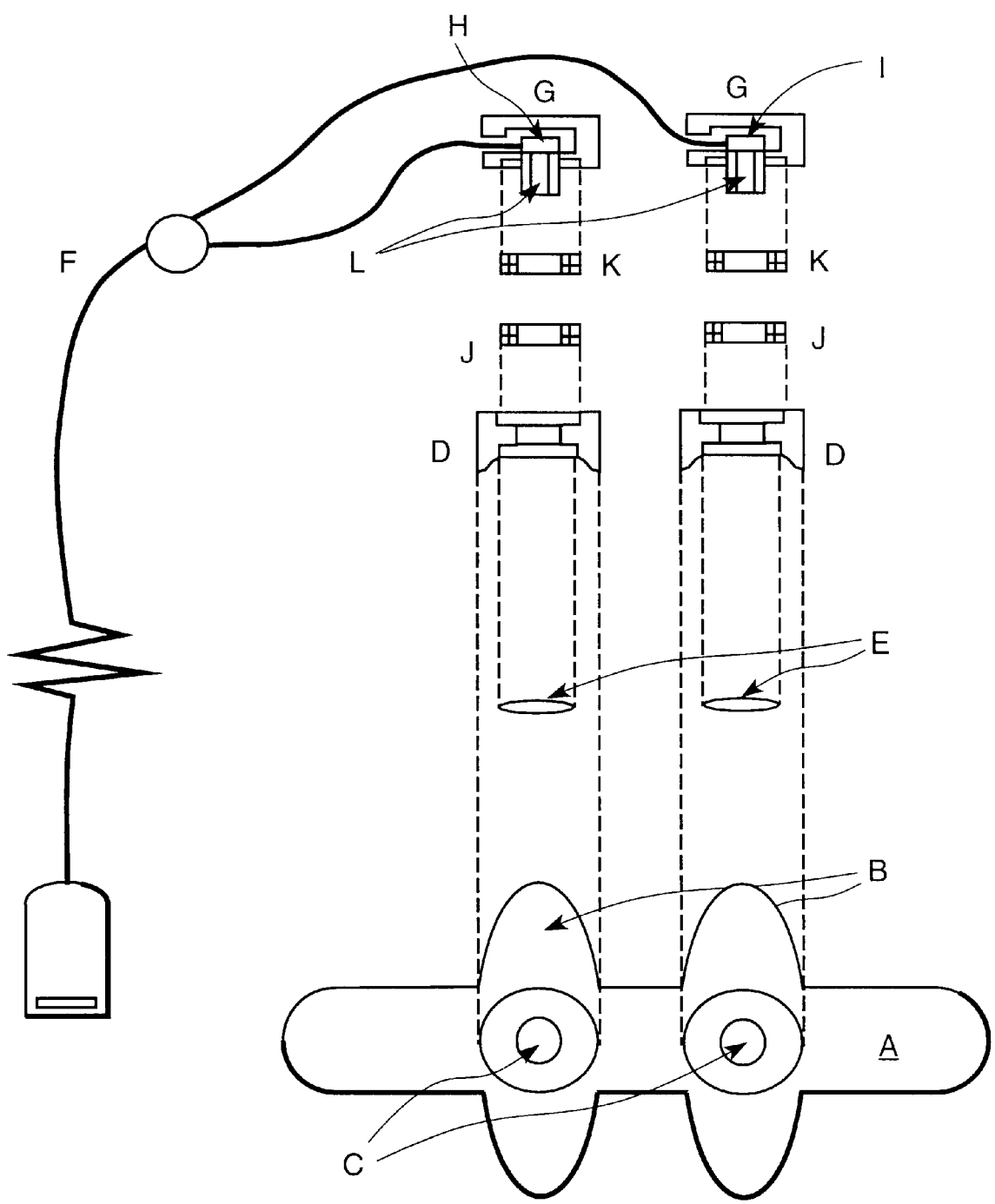
FIG. 1 is an exploded view of the reusable pulse oximeter probe and disposable bandage apparatus incorporating the invention.

The Reusable Pulse Oximeter Sensor constitutes a "Y" style pulse oximeter probe shown as FIG. 1, Item F. Said probe incorporates two plastic housings shown as FIG. 1, Items G, said housings containing apertures or radiation transparent windows therein, said apertures or windows shown as FIG. 1, Items L. One housing contains the light emitting diode of the probe, FIG. 1, item H, and the other contains the photocell detector, FIG. 1, Item I. The emitter and detectors are aligned with the apertures or windows of said housings in order to transmit and receive light through a human appendage. Seated within a recessed area of each housing, and attached permanently thereto, is a "mushroom hook" adhesive-backed pad, FIG. 1, Item K. The purpose of these pads is to selectively engage the "mushroom hook" pads, FIG. 1, Items J, attached permanently to the plastic discs, FIG. 1, Items D, and to attach the reusable probe assembly to the Disposable Bandage Apparatus. The Reusable Pulse Oximeter Sensor is shown assembled as FIG. 2, Item A.

In another embodiment of the invention the light emitting diode and photocell detector of the reusable pulse oximeter sensor are enclosed in housings (FIG. 5, Items A) having a groove on the inner diameter of the housings that is designed to matedly engage rings (FIG. 5, Items B) located on the outer diameter of the disposable bandage apparatus, thus securing and locking the sensor housings to the bandage receptacles.

Figure 6:
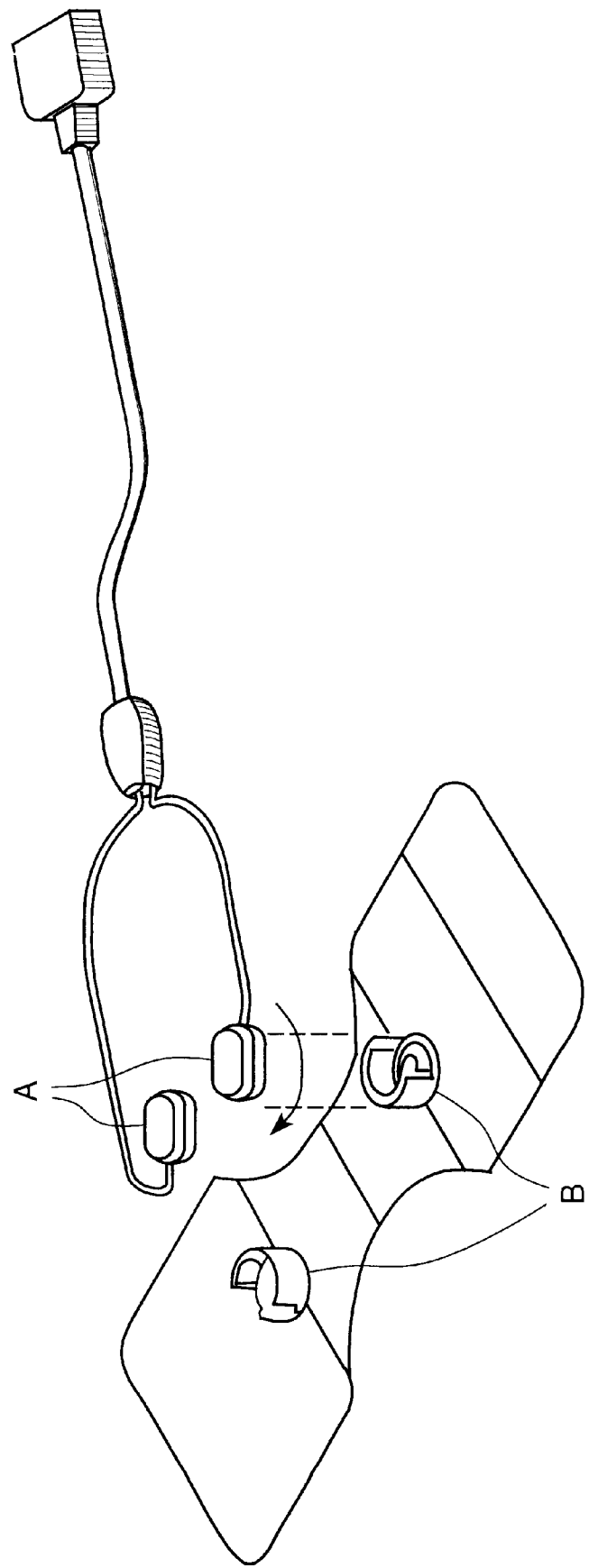
FIG. 6 illustrates an assembled view of another embodiment of the invention in which the housings of the pulse oximeter probe are affixed to the receptacles of the disposable bandage apparatus by means of "twist and lock" type connectors.

In another embodiment of the invention the light emitting diode and photocell detector of the reusable pulse oximeter sensor are enclosed in housings (FIG. 6, Items A) which are designed to enter the bandage receptacles (FIG. 6, Items B) and to twist 90 degrees thus locking the sensor housings to the bandage receptacles.

In yet another embodiment of the invention, the light emitting diode and photocell detector of the reusable pulse oximeter sensor are enclosed in housings (FIG. 7, Items A) having a threaded flange (FIG. 7, Items B) that threadedly engages the bandage receptacles, (FIG. 7, Items C) thus securing and locking the sensor housings to the bandage receptacles.

Figure 8:
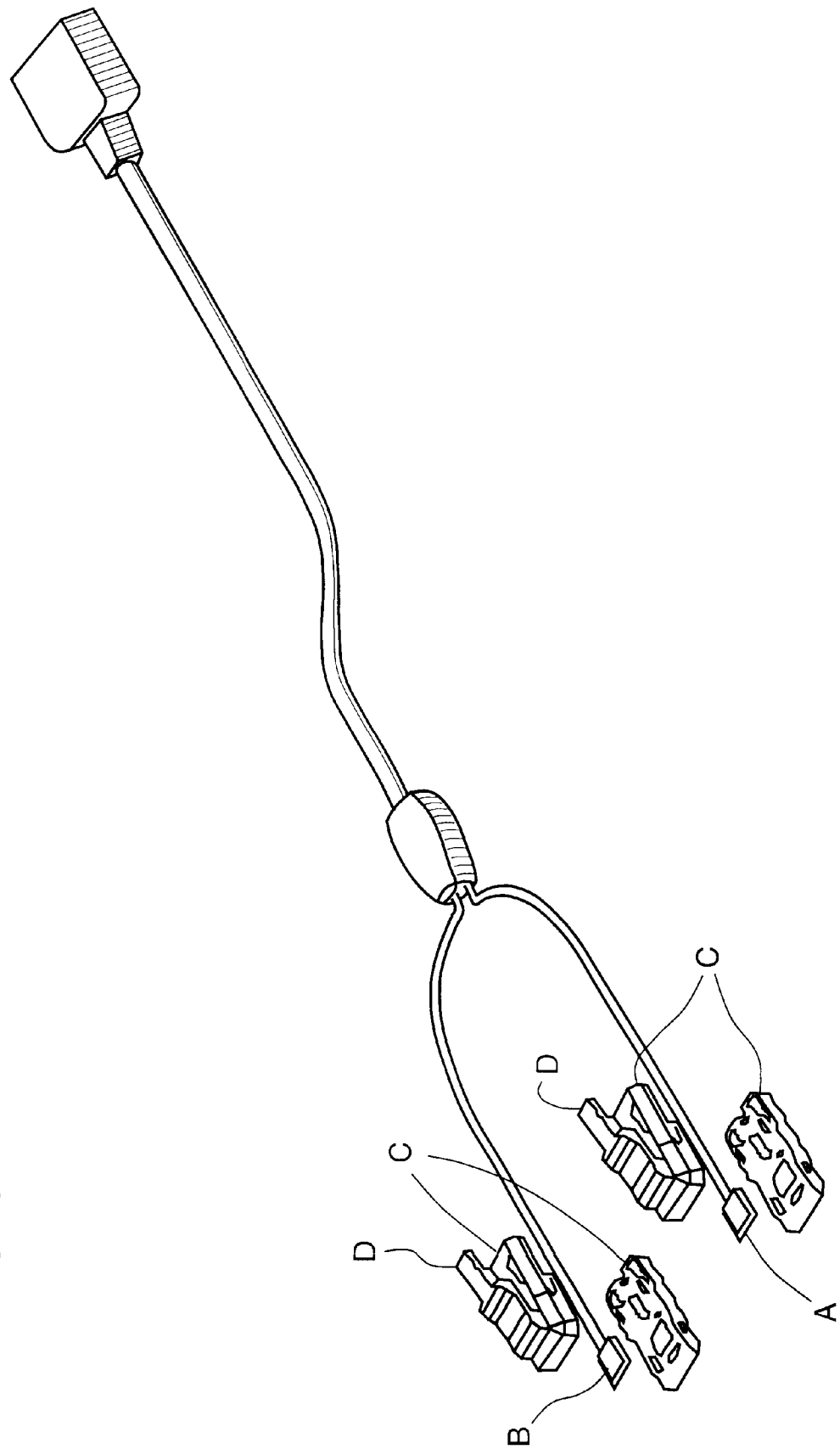
FIG. 8 illustrates an exploded view of the first preferred embodiment of the reusable pulse oximeter probe in which the light emitting diode and photocell detector of the probe are encased in housings having a radiation transparent window therein and locking levers for affixing the reusable pulse oximeter probe to the disposable bandage apparatus.
Figure 9:
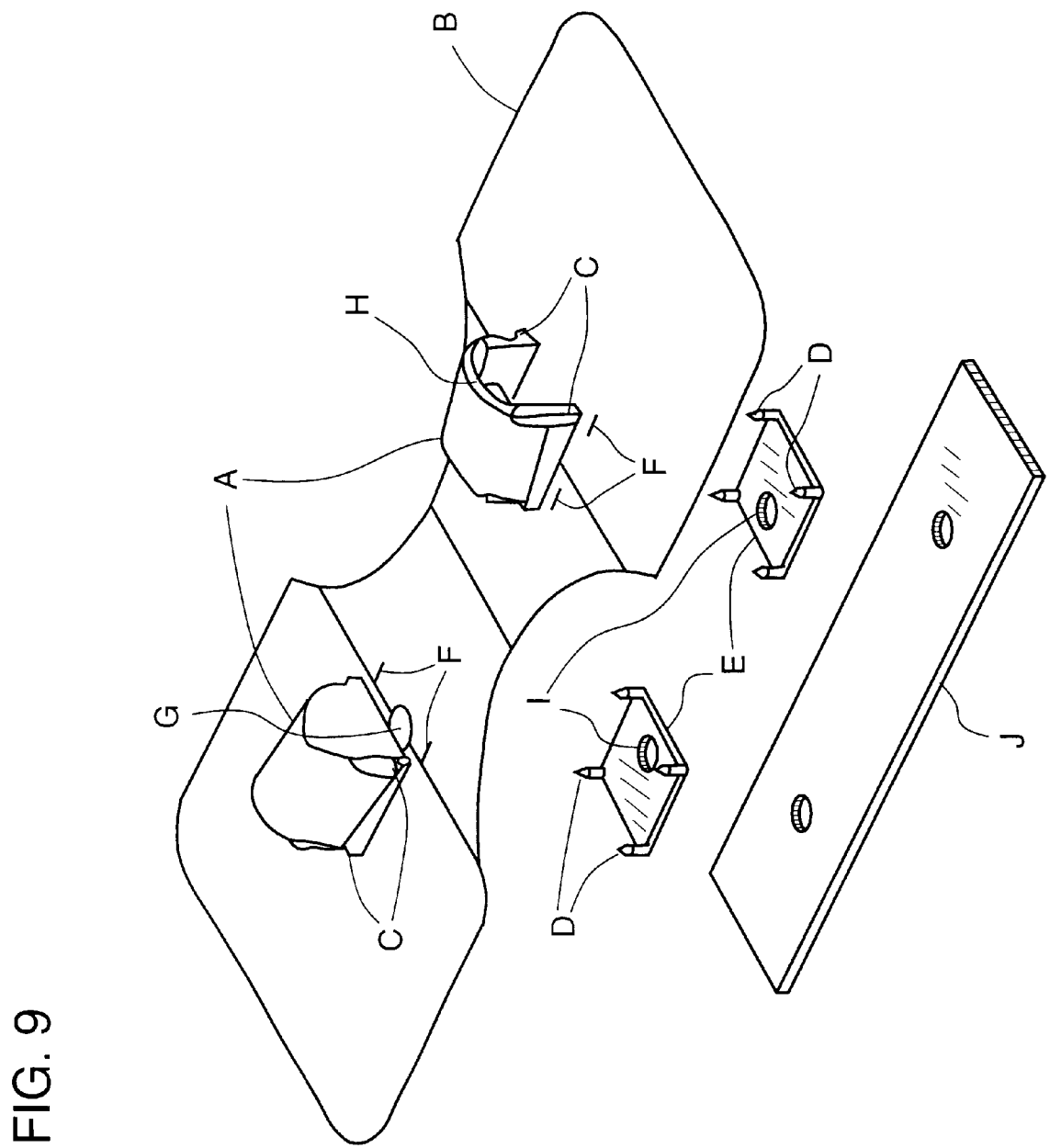
FIG. 9 illustrates an exploded view of the first preferred embodiment of the disposable bandage apparatus in which the receptacle tops incorporate a slot for engaging the locking levers of the modular probe housings, and wherein the radiation transparent windows are mounted on the opposite side of the bandage strip thus sandwiching and securing the bandage in between the two receptacle halves by means of locking tabs or heat stakes that can be ultrasonically welded.

In the first preferred embodiment of the Reusable Pulse Oximeter Sensor, the light emitting diode (FIG. 8, Item A) and photocell detector (FIG. 8, Item B) of the probe assembly are housed in modular receptacles (FIG. 8, Items C)

having locking levers, (FIG. 8, Items D) for engaging the receptacles (FIG. 9, Items A) of the disposable bandage apparatus, and locking them into place.

Figure 11:
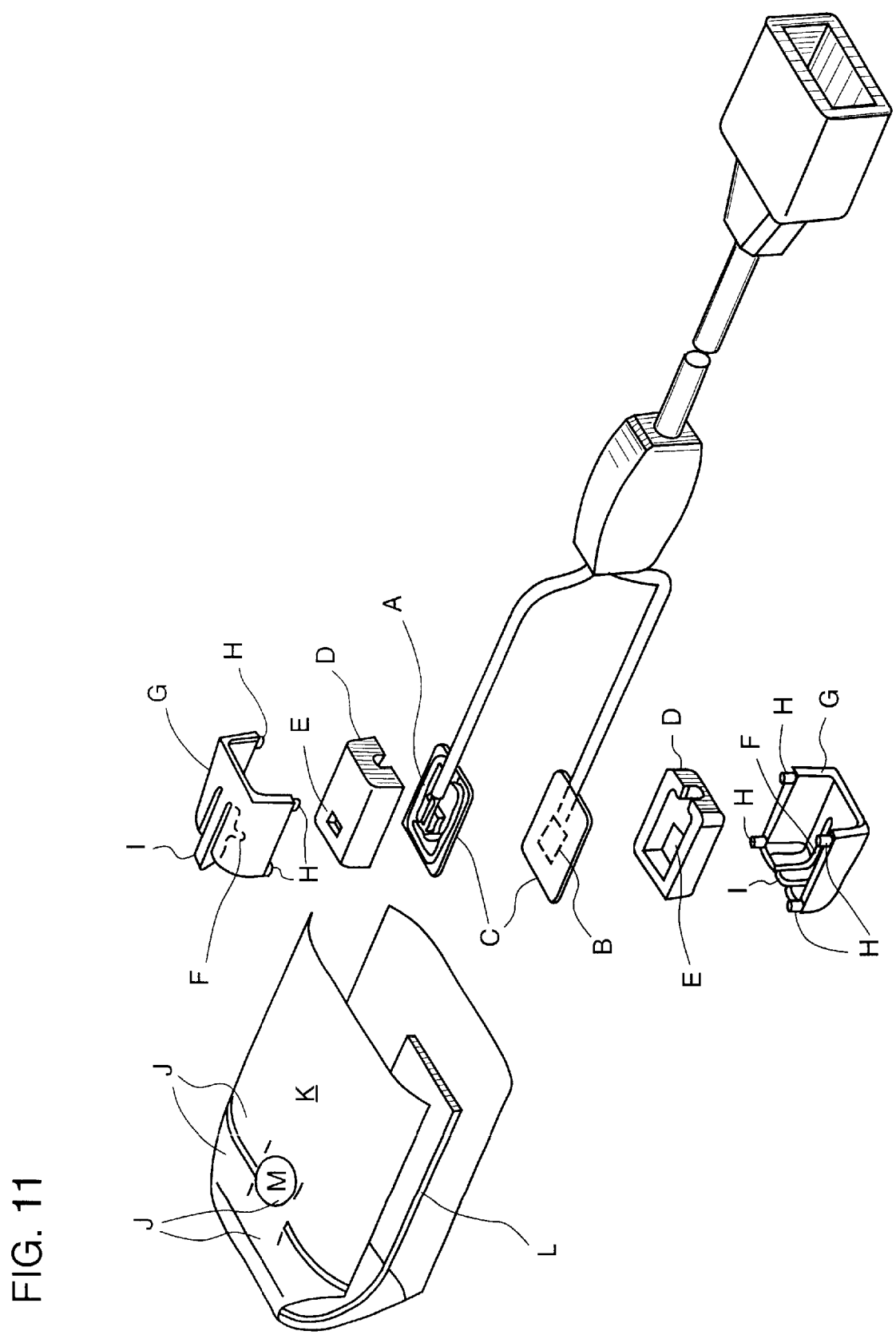
FIG. 11 illustrates an exploded view of the second preferred embodiment of the invention in which the probe housings have a slot or indentation incorporated therein and the bandage receptacles have a locking lever for securing the housings to the receptacles.

In the second preferred embodiment of the Reusable Pulse Oximeter Sensor, the light emitting diode (FIG. 11, Item A) and the photocell detector (FIG. 11, Item B) are encased in modular housings having a radiation transparent bottom (FIG. 11, Items C) and having opaque housing tops (FIG. 11, Items D). These housing tops and bottoms are ultrasonically welded together thus encapsulating the light emitting diode and photocell detector of the probe assembly. The housing tops incorporate indentations or slots (FIG. 11, Items E) designed to matedly engage a protrusion on the locking levers of the bandage receptacles thus snapping into place and securing the probe housings within the bandage receptacles.

Description of the Disposable Bandage Apparatus

The components of the apparatus include an adhesive-backed, strip, shown as FIG. 1, item A, said strip incorporating two oval protrusions centered thereon and shown as FIG. 1, Item B. Said strip also incorporates two apertures, centrally located within said oval protrusions, FIG. 1, Item C, each aperture having a diameter sufficient in size to accommodate the transmission and reception of light from a light emitting diode and photocell detector of a pulse oximeter probe.

On top of said apertures are seated two plastic discs, FIG. 1, Item D, each having a concave base designed to conform to the radius of a human digit, and an aperture of slightly larger diameter than the apertures in the adhesive backed planar strip. Said plastic discs are affixed to the adhesive planar strip by means of a permanent adhesive. Seated in a recessed area on top of each plastic disc is a "mushroom hook", adhesive backed pad shown as FIG. 1, Item J. The purpose of the "mushroom hook" pads is to selectively engage the "mushroom hook" pads attached to the probe, FIG. 1, Items K, and to attach the probe to the disposable bandage apparatus. Sandwiched between the two plastic discs and the planar adhesive strip are two translucent silicone windows, FIG. 1, Item E. Said windows are designed to permit the passage of infrared light and yet prevent contact between probe and patient, and consequently, contamination of the reusable probe itself.

Figure 2:
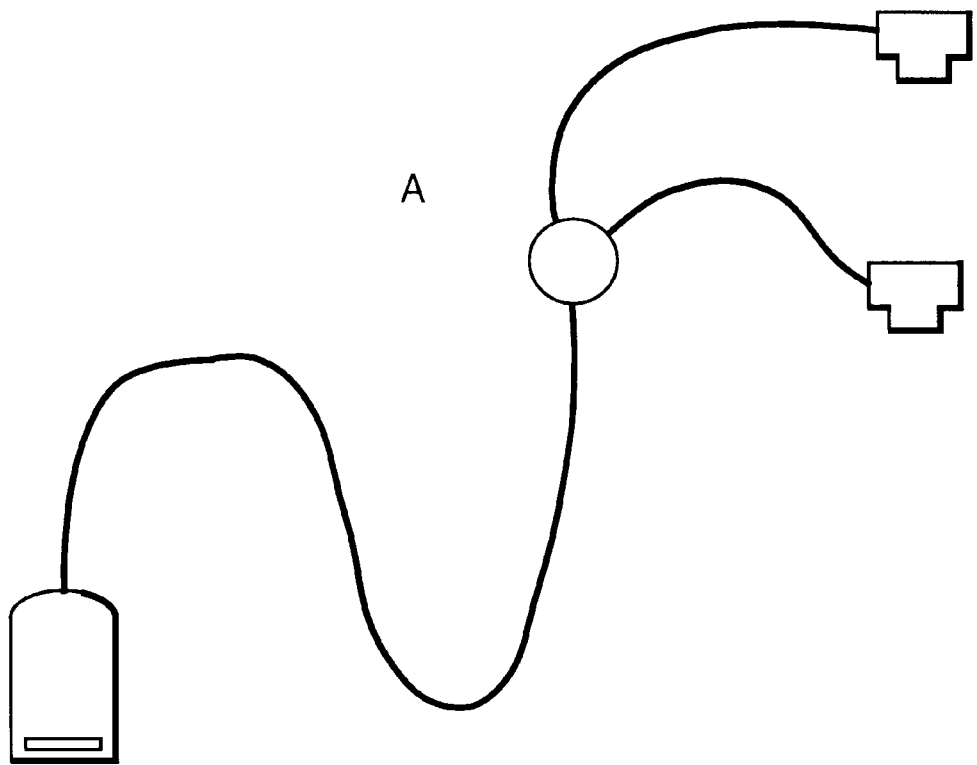
FIG. 2 is a view of the reusable pulse oximeter probe and disposable bandage apparatus shown individually as components of the invention.
Figure 2:
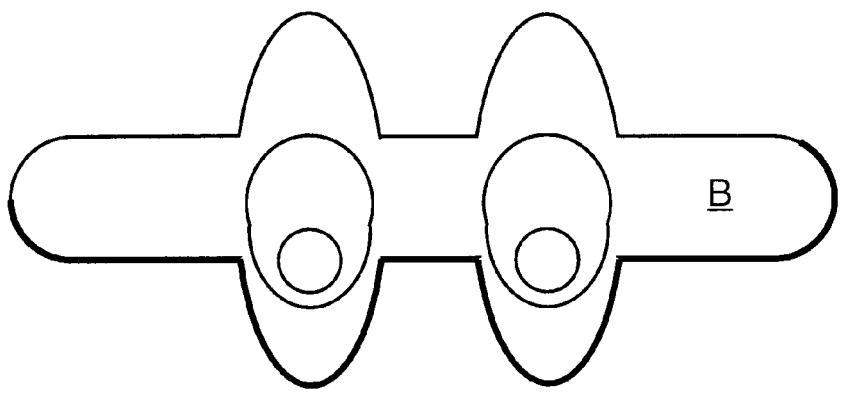

The above items constitute the Disposable Bandage Apparatus of the invention, said apparatus being shown assembled as FIG. 2, Item B.

Figure 4:
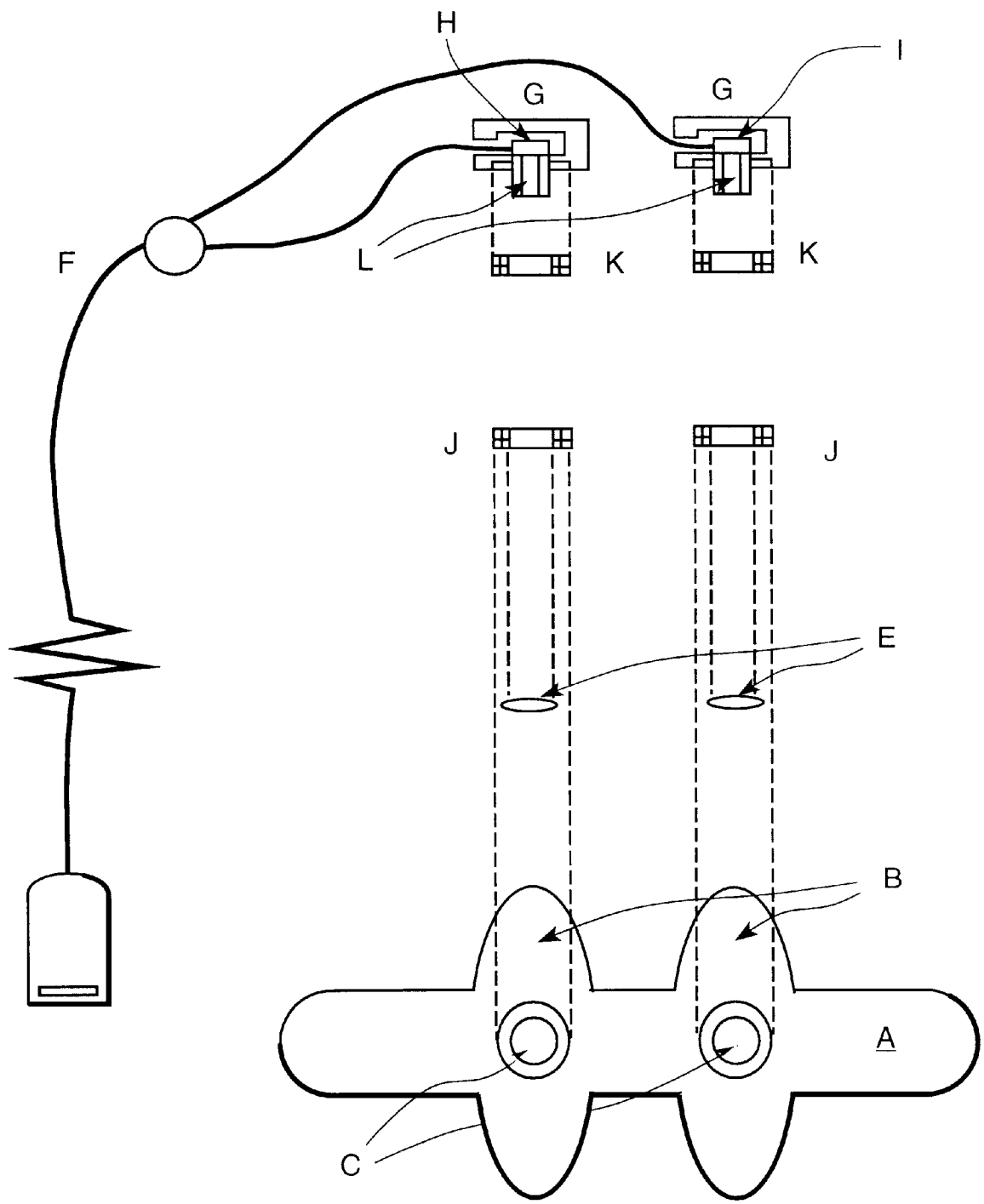
FIG. 4 illustrates an exploded view of another embodiment of the invention in which the "mushroom hook" material itself is used as the receptacle of the disposable bandage apparatus.

In another embodiment of the invention, the Disposable Bandage Apparatus may be configured as in FIG. 4 of the drawings. In that drawing there is an exploded view of the apparatus in which the "mushroom hook" pads of the bandage apparatus, FIG. 4, Items J, are bonded directly to the adhesive planar strip, FIG. 4, Item A, for the selective engagement of the "mushroom hook" pads of the probe, FIG. 4, Items K, said pads being attached permanently to the housings of the probe, FIG. 4, Items G.

Figure 5:
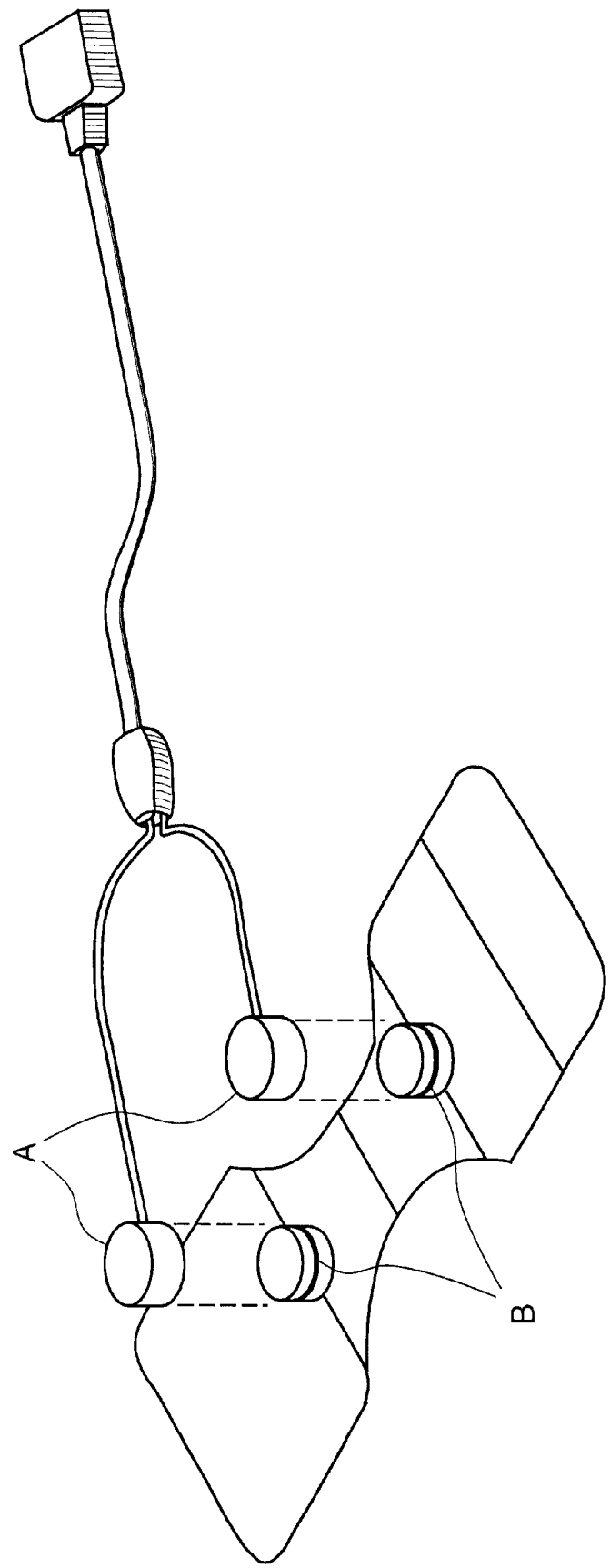
FIG. 5 illustrates an assembled view of another embodiment of the invention in which the housings of the pulse oximeter probe are affixed to the receptacles of the disposable bandage apparatus by means of ring and groove type, snap-on connectors.
Figure 7:
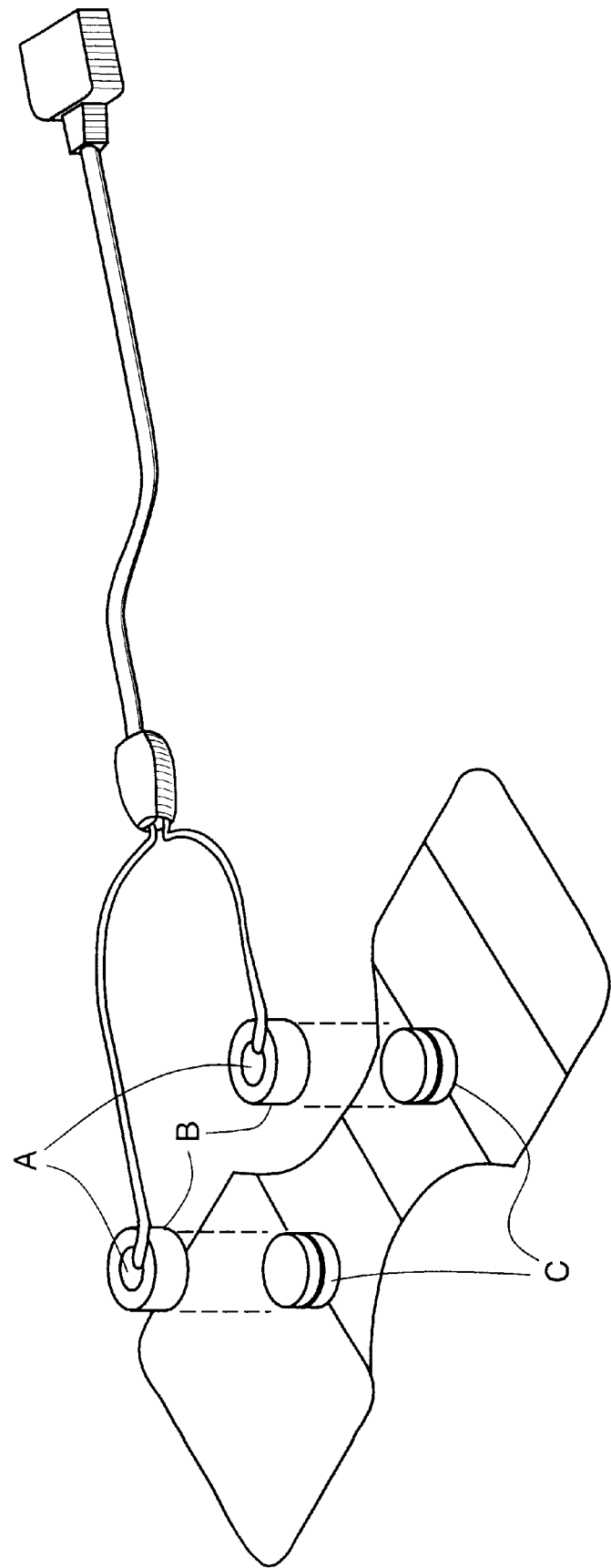
FIG. 7 illustrates an assembled view of another embodiment of the invention in which the housings of the of the pulse oximeter probe are affixed to the receptacles of the disposable bandage apparatus by means of a "threaded flange" type of connector.

In other embodiments of the disposable bandage apparatus, the bandage may have mounted thereon receptacles having means of matedly engaging the housings of the reusable pulse oximeter sensor by way of "ring and groove"snap-on type connectors (FIG. 5, Items B); "Twist and Lock" type connectors (FIG. 6, Items B); or "threaded flange" type connectors (FIG. 7, Items C).

In the first preferred embodiment of the Disposable Bandage Apparatus, the bandage strip (FIG. 9, Item B) is sandwiched between interlocking receptacle halves. The top halves of the receptacles (FIG. 9, Items A) each contain 4 holes (FIG. 9, Items C) that are designed to matingly engage locking tabs (FIG. 9, Items D) on the bottom half of the receptacles (FIG. 9, Items E) that are pushed through slots cut in the bandage strip (FIG. 9, Items F) thus securing and locking the bandage in between.

Figure 10:
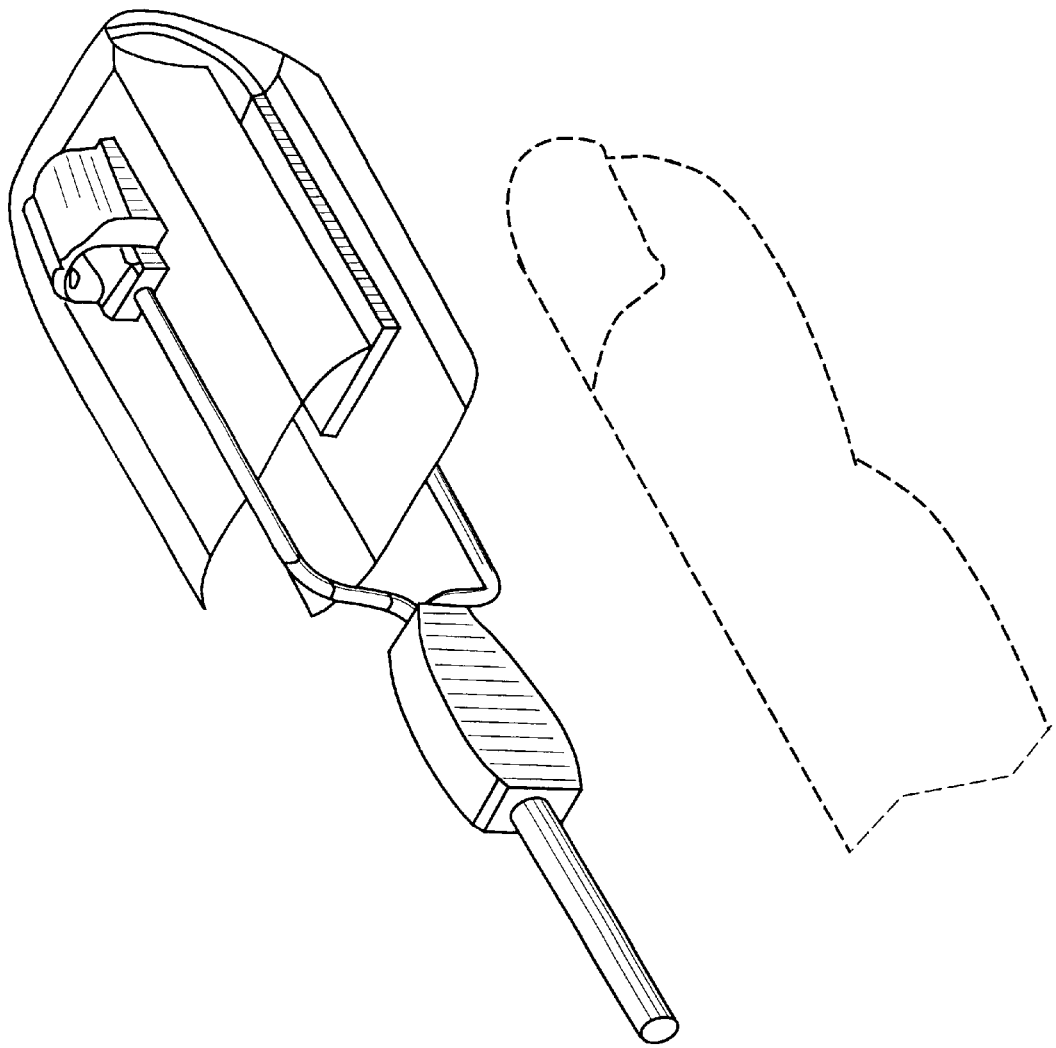
FIG. 10 illustrates the first preferred embodiment of the invention as it would appear ready for use on a human digit.

The bandage strip contains two apertures or radiation transparent windows (FIG. 9, Items G) allowing for the transmission and reception of light from the light emitting diode and photocell detector of the pulse oximeter sensor which are encased in modular housings having locking levers (FIG. 8, Items D) wherein said levers engage slots in the receptacles (FIG. 9, Items H) thereby locking the housings into place within the receptacles. In addition, the bottom halves of the receptacles (FIG. 9, Items E) can be of a radiation transparent material, or may contain apertures (FIG. 9, Items I) thus allowing the light emitting diode and photocell detector contained in the probe housings, when engaged in the bandage receptacles, to transmit and receive light through the apertures of the bandage strip and through the radiation transparent material, or apertures, of the bottom halves of the receptacles, and through the appendage of a patient. The disposable bandage apparatus may also incorporate a foam strip (FIG. 9, Item J) in order to cushion a patient's appendage from any discomfort caused by the bottom half of the bandage receptacles. The complete Reusable Pulse Oximeter Sensor, engaged in the disposable Bandage Apparatus, and ready for use on a human appendage, is shown in FIG. 10.

In the second preferred embodiment of the disposable bandage apparatus, the bandage receptacles (FIG. 11, Items G) are secured to the bandage (FIG. 11, Item K) by means of four protrusions or "heat Stakes" (FIG. 11, Items H) which are pushed through slots (FIG. 11, Items J) on the bandage (FIG. 11, Item K) and are ultrasonically welded on the other side, thus securing the receptacles to the bandage. A radiation transparent window (FIG. 11, Item M) is then adhered to the underside of the bandage and the radiation transparent windows and melted heat stakes are then overlaid by a foam pad (FIG. 11, Item L) to aid in patient comfort. This foam pad also incorporates two holes which are in alignment with the two holes on the bandage itself, and when the foam pad is overlaid on the underside of the bandage, the radiation transparent windows are sandwiched in between.

Figure 12:
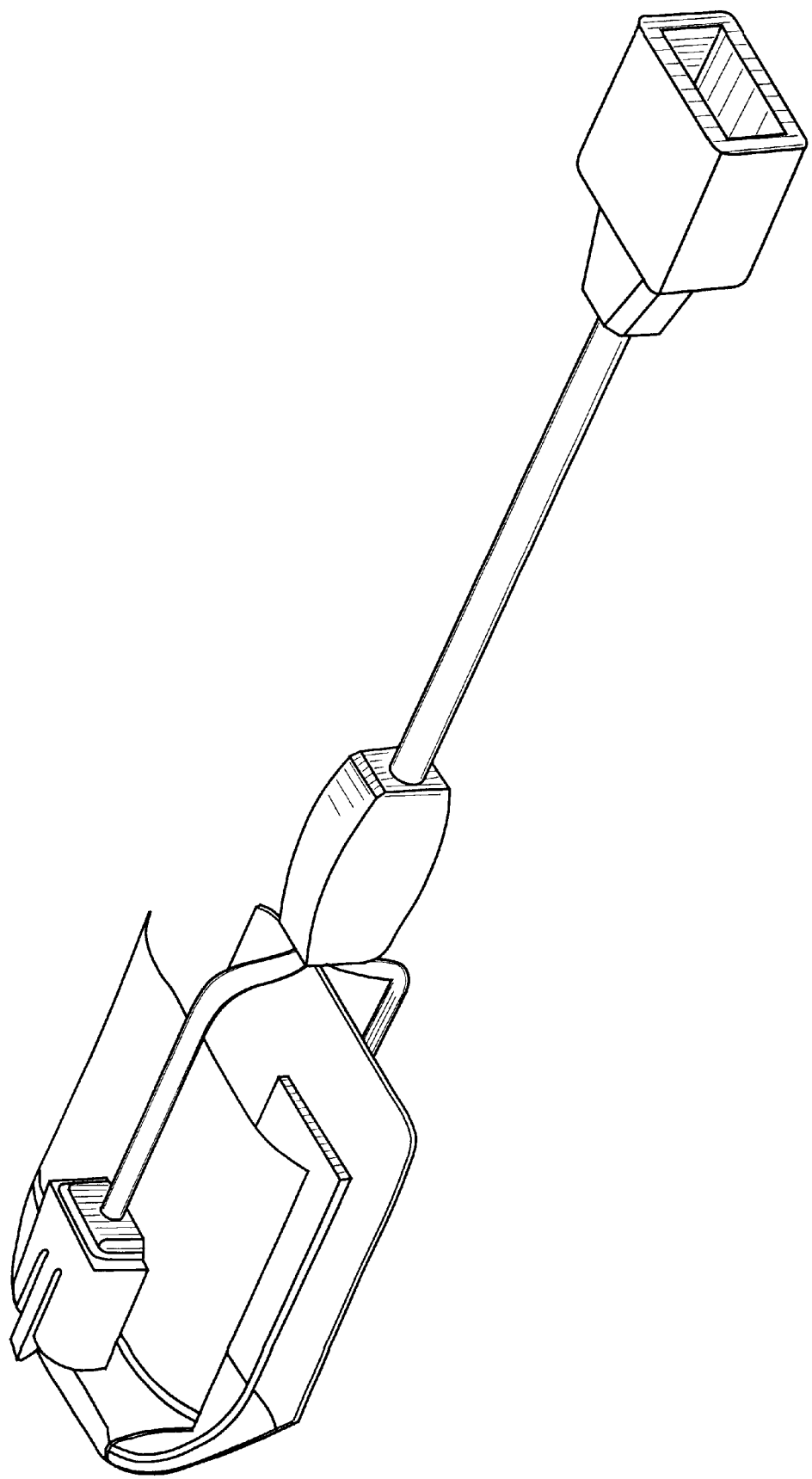
FIG. 12 illustrates an assembled view of the second preferred embodiment of the invention in which the probe housings have a slot or indentation incorporated therein and the bandage receptacles have a locking lever for securing the housings to the receptacles.

The probe housings are designed to matedly engage the bandage receptacles (FIG. 11, Items G) and are held in place within the receptacles by means of protrusions (FIG. 11, Items F) on the locking levers (FIG. 11, Items I) which snap into place when the probe housings are pushed into the bandage receptacles. When the probe housings are locked into place within the bandage receptacles the light emitting diode and photocell detector are in alignment with the holes in the bandage and the foam overlay, and the probe is then able to transmit and receive light through the mated housings and receptacles, through the holes contained in the bandage and foam overlay, and through the appendage of a patient. The complete assembled Reusable Pulse Oximeter Sensor engaged within the Disposable Bandage Apparatus, as it would appear ready for use on a patient, is shown in FIG. 12.

Other Fastening Means

As can be appreciated there are many ways of fabricating the above components of the invention. The above description describes attachment of the Reusable Pulse Oximeter Sensor to the Disposable Bandage Apparatus by way of a "mushroom hook" type hook and loop material, by the use of "ring and groove" type snap-on connectors, "push and twist" type Luerlock connectors, and threaded flange type connectors' as well as telephone type, modular connectors and receptacles. While these means are fairly comprehensive, they should in no way be considered exhaustive.

Method of Use

Figure 3:
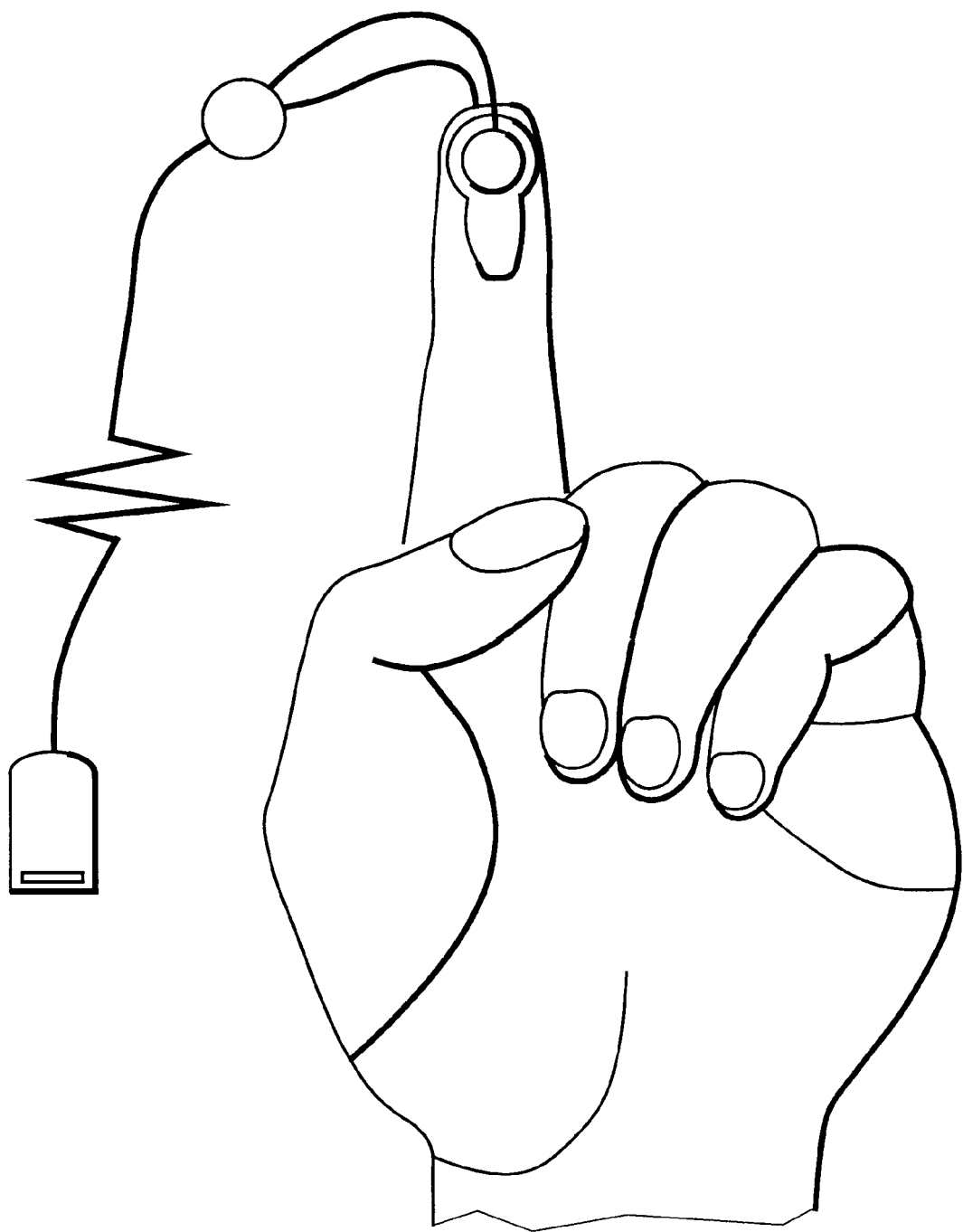
FIG. 3 illustrates the invention in use on a human finger or digit.

For use on each individual patient, the probe is affixed in the following manner:

Firstly, the backing is removed from the adhesive strip of the Disposable Bandage Apparatus. One of the apertures of the apparatus is visually positioned on the center of the nail bed of the patient's appendage and one side of the adhesive strip and the oval protrusions are adhered to the patient's digit. The rest of the strip is then looped over the end of the patient's appendage, and the plastic disc is aligned so as to exactly oppose the plastic disc already attached to the other side of the digit. Once the Disposable Bandage Apparatus has been properly adhered to the patient, the plastic housings of the probe assembly can be easily snapped into place on opposing sides of the digit. The entire assembled probe is shown as it would appear in use on a patient in FIG. 3.

For use with the "ring and groove" type snap-on connectors, "twist and lock", and "threaded flange" connectors, the backing is firstly removed from the adhesive strip. The strip is then folded in half where indicated on the bandage and the bandage apparatus is adhered to either side of the human digit. Once the bandage apparatus is in place the probe housings are simply snapped, twisted or screwed into place.

For use with each patient, the modular probe and bandage assembly, in both of its embodiments, which are the preferred embodiments of the invention, would be attached as follows:

Firstly, the backing is removed from the adhesive strip. The strip is then folded where indicated on the bandage and the strip is then adhered to opposing sides of the human digit. Once the bandage apparatus is in place, the housings of the probe are pushed into the receptacles and locked in place by means of the locking levers.

In all embodiments of the invention, when the probe is no longer required on the patient, the housings of the Reusable Probe are simply unsnapped from the Disposable Bandage Apparatus, the bandage apparatus is thrown away, and the probe can then be reused on a new patient in conjunction with a new bandage apparatus.

Advantages of the Present Invention

Current reusable pulse oximeter probes are either "Clam Shell" type clamping devices which can restrict circulation or "Y" type probes which are taped directly to the patient. Both types also come in direct contact with the patient's skin and bodily fluids and need sterilization after use. Because of the fact that these devices incorporate many surfaces and at times, porous materials, proper sterilization is very difficult. With the present invention there is no contact between the reusable probe and the skin or bodily fluids of the patient.

Disposable probes are very costly because of the fact that the cable, connectors and photodiodes are all disposed of after use. The present invention accomplishes the same goals as a disposable probe from a cleanliness standpoint, but since only the attachment apparatus is discarded after use, the cost is much less to a healthcare institution.

The present invention, with the concave shape of the plastic discs of the bandage apparatus, when backed by the adhesive strip, is extremely effective in preventing the entrance of extraneous light from the sides of the patient's digit. Current probes on the market, whether disposable or reusable, because of the nature of their shape and affixation means, have problems in dealing with extraneous light reception.

The present invention utilizes an easy snap on, snap off, or modular connector attachment means for attaching the probe to the Disposable Bandage Apparatus. Probe-Shield type devices available in the past not only required the modification of the original manufacturer's probe, but required the difficult procedure of inserting a flexible laminated probe into a sheath for each patient.

Probe-Shield devices, because of the lamination process involved, raised some concern over the transmission and reception of infrared light through the laminating material. The present invention uses a silicone window for the isolation of the probe from the patient. Infrared light transmission and reception is not affected by passage through translucent silicone.

In these days of environmental consciousness the annual waste generated from tens of millions of disposable probes is enormous. The present invention, if used in considerable numbers, would greatly reduce the amount of environmental waste generated by disposable pulse oximeter probes.

While the invention has been described in relation to preferred embodiments of the invention, it will be appreciated that other embodiments, adaptations and modifications of the invention will be apparent to those skilled in the art.

What is claimed is:

1. A reusable pulse oximeter sensor and disposable bandage apparatus, comprising:
    a) a reusable pulse oximeter probe assembly with at least one light emitting diode and one photocell detector wherein said detector and emitter are incorporated into plastic housings, one housing having an aperture or radiation transparent window aligned with said emitter and the other housing having an aperture or radiation transparent window aligned with said detector;
    b) at least one bandage strip having adhesive on at least a portion of at least one face thereof and at least two receptacles mounted thereon, each receptacle having at least one aperture or radiation transparent window located therein;
    wherein said probe housings can matedly engage said bandage receptacles, and transmit and receive light through the apertures or radiation transparent windows of said mated housings and receptacles, and through the appendage of a patient.

2. The reusable pulse oximeter sensor and disposable bandage apparatus of claim 1 wherein said reusable pulse oximeter probe housings are made from a material selected from plastic, rubber, metal, wood, or other composite material.

3. The reusable pulse oximeter sensor and disposable bandage apparatus of claim 1 wherein said bandage receptacles are made from a material selected from plastic, rubber, metal, wood, or other composite material.

4. The reusable pulse oximeter sensor and disposable bandage of claim 1 wherein translucent silicone or other radiation transparent windows are sandwiched between said adhesive strip and said receptacles attached thereto.

5. The reusable pulse oximeter sensor and disposable bandage of claim 1 wherein said housings have tubular protrusions and the apertures of said receptacles are large enough to accept the tubular protrusions of said housings for the purpose of concentric location of the housings to the receptacles and the proper transmission of light therethrough.

6. The reusable pulse oximeter sensor and disposable bandage of claim 1 wherein said bandage apparatus may be discarded after single patient use and said reusable probe may be used again on another patient in conjunction with a new bandage apparatus.

7. The reusable pulse oximeter sensor and disposable bandage of claim 1 wherein said receptacles have a concave shape on one side thereof in order to seat conformably on a human digit.

8. The reusable pulse oximeter sensor and disposable bandage of claim 1 wherein said receptacles have a flat surface on at least one side thereof in order to seat conformably on a human ear, nose, or foot.

9. The reusable pulse oximeter sensor and disposable bandage of claim 1 wherein the housings and receptacles contain "mushroom hook" type hook and loop material for the purpose of adhering and detaching said housings to and from said receptacles.

10. The reusable pulse oximeter sensor and disposable bandage of claim 9 wherein the housings and receptacles have recessed areas for adhesion of the "mushroom hook" hook and loop material.

11. The reusable pulse oximeter sensor and disposable bandage of claim 9 wherein the receptacles of said disposable bandage are the "mushroom hook" material itself.

12. The reusable pulse oximeter probe and disposable bandage of claim 1 including attachment means for securing said probe housings to said bandage receptacle comprising a "ring and groove" snap-on type connector.

13. The reusable pulse oximeter probe and disposable bandage of claim 1 including attachment means for securing said probe housings to said bandage receptacles comprising a "twist and lock" type connector.

14. The reusable pulse oximeter probe and disposable bandage of claim 1 wherein the attachment means for securing said probe housings to said bandage receptacles comprises a "threaded flange" type connector.

15. The reusable pulse oximeter probe and disposable bandage of claim 1 including a locking mechanism comprising at least one notch, slot, or indentation in at least one of said bandage receptacles, for matedly engaging a locking lever or tab of at least one of said pulse oximeter probe housings.

16. The reusable pulse oximeter probe and disposable bandage of claim 1 including a locking mechanism comprising at least one tab or lever on at least one of said receptacles, for matedly engaging a slot or indentation in at least one of said pulse oximeter probe housings.

17. The reusable pulse oximeter probe and disposable bandage of claim 15 wherein said bandage incorporates a foam strip or strips for patient comfort.

* * * * *